United States Patent
Anitua Aldecoa

(10) Patent No.: US 11,744,917 B2
(45) Date of Patent: Sep. 5, 2023

(54) TISSULAR FORMULATION OR ADHESIVE OBTAINED FROM A BLOOD COMPOSITION CONTAINING PLATELETS, AND METHOD FOR THE PREPARATION OF SAID FORMULATION

(71) Applicant: BIOTECHNOLOGY INSTITUTE, I MAS D, S.L., Vitoria (ES)

(72) Inventor: Eduardo Anitua Aldecoa, Vitoria (ES)

(73) Assignee: BIOTECHNOLOGY INSTITUTE, I MAS D, S.L., Vitoria (ES)

( * ) Notice: Subject to any disclaimer, the term of this patent is extended or adjusted under 35 U.S.C. 154(b) by 446 days.

(21) Appl. No.: 16/787,190

(22) Filed: Feb. 11, 2020

(65) Prior Publication Data

US 2020/0254138 A1    Aug. 13, 2020

(30) Foreign Application Priority Data

Feb. 11, 2019   (ES) ................ ES201930106

(51) Int. Cl.
| | |
|---|---|
| *A61L 24/10* | (2006.01) |
| *A61L 24/00* | (2006.01) |
| *A61L 24/04* | (2006.01) |

(52) U.S. Cl.
CPC ......... *A61L 24/106* (2013.01); *A61L 24/0015* (2013.01); *A61L 24/043* (2013.01); *A61L 2300/414* (2013.01)

(58) Field of Classification Search
CPC .. A61L 24/106; A61L 24/0015; A61L 24/043; A61L 2300/414
See application file for complete search history.

(56) References Cited

U.S. PATENT DOCUMENTS

| 6,569,204 B1 | 5/2003 | Anitua Aldecoa | |
| 2015/0037430 A1* | 2/2015 | Anitua Aldecoa | A61K 35/16 424/530 |

FOREIGN PATENT DOCUMENTS

| ES | 2221770 A1 | 1/2005 |
| ES | 2369945 A1 | 12/2011 |
| WO | WO 2010/142784 | * 12/2010 |

* cited by examiner

*Primary Examiner* — Shirley V Gembeh
(74) *Attorney, Agent, or Firm* — BROWDY AND NEIMARK, PLLC

(57) ABSTRACT

A formulation, or tissular adhesive, obtained from a platelet-rich blood composition and/or growth factors, and method for the preparation of this adhesive. The preparation method of the adhesive comprises the steps of raising the temperature of the initial blood composition and subsequently activating the composition. Among other advantages, the tissular adhesive is biocompatible and biodegradable, has desirable biological or medical properties provided by the presence of platelets or growth factors, and also has a high adhesiveness and an accelerated coagulation process.

11 Claims, 3 Drawing Sheets

TISSULAR FORMULATION OR ADHESIVE OBTAINED FROM A BLOOD COMPOSITION CONTAINING PLATELETS, AND METHOD FOR THE PREPARATION OF SAID FORMULATION

TECHNICAL FIELD

The invention relates to a formulation with desirable biological or medical properties, obtained from an initial blood composition containing platelets. The invention also relates to a method for preparing this formulation. The formulation serves as a tissular adhesive.

STATE OF THE ART

The preparation of compositions from human or animal blood is known in the prior art, wherein blood is processed so that a platelet-rich plasma (PRP) and/or a plasma rich in growth factors with useful biological and medical properties is obtained. Such PRP or plasma rich in growth factors have been used successfully in ex vivo applications, for example as a cell culture medium, and in vivo, for example to carry out a bone regeneration process in a patient or to treat a patient with a joint ailment using infiltrations. In the case of compositions intended for in vivo applications, the technology for the preparation of PRP formulations and plasma rich in growth factors has evolved towards the preparation of autologous compositions, i.e. obtained from the patient's own blood. Examples of these compositions and preparation methods can be found in the U.S. Pat. No. 6,569,204 and ES2221770.

Moreover, compositions consisting of platelet-rich fibrin (PRF), obtained from blood, are also known. Like the aforementioned plasmas, fibrin can be autologous or heterologous. Unlike plasma, which is liquid, fibrin has a solid or semi-solid consistency.

One example of fibrin is known as fibrin gel or fibrin mesh, which is a formulation whose semi-solid consistency is very useful for certain applications. The preparation procedure of the fibrin gel or mesh generally begins with a first phase in which a PRP or plasma rich in growth factors is obtained by an applicable method, for example by centrifuging blood taken from a patient until the blood separates into several fractions, and extracting the upper fraction, i.e. the fraction of platelet-rich plasma (PRP) or plasma rich in growth factors. Subsequently, the platelets contained in the PRP or plasma rich in growth factors are activated (activation herein being understood as the action of causing the platelets to release certain growth factors contained within them), for example by the addition of calcium chloride. As a consequence of the activation, and after waiting long enough, the eventual polymerization of fibrin is produced from the fibrinogen contained in the plasma, obtaining a final compound that is a fibrin clot (also called fibrin gel or mesh because of its semi-solid consistency, like a kind of biological sponge). This procedure is usually performed to obtain fibrin gel from blood that has been modified with an anticoagulant, such as sodium citrate. However, blood can also be processed without mixing it beforehand with anticoagulant; in this case, by centrifuging the blood, it is possible both to separate the plasma from the red blood cells and at the same time obtain the fibrin gel without the need to add calcium chloride or any other platelet activator. Some examples of application of the fibrin gel or mesh include the following: to form a biological scaffolding to fill bone defects; to be applied to wounds or injuries for the progressive release of growth factors; to be used as a matrix for stem cell culture; to be used as a membrane to close defects or ulcers; to be used in the manufacture of tissues, known as tissue engineering, wherein in addition to cells and growth factors it is especially important to have a matrix or scaffold where the cells can grow.

However, platelet-rich preparations (PRP, plasma rich in growth factors, PRF) have a limited capacity as tissular adhesive. The importance of having good adhesive properties is great, as surgical and chronic wounds represent a worldwide socioeconomic burden, both for patients and for health systems, which is often underestimated. One of the main concerns that we find at this level is profuse, continuous haemorrhaging which can occur during surgery or in a chronic wound, and the postoperative discomfort and complications derived from surgical sutures, such as suture abscesses, the formation of granulomas or tissue necrosis. Over the years, a wide range of treatment modes have emerged in the world of surgery with the aim of reducing such complications, among them the use of fibrin glue/sealant.

Commercial allogeneic fibrin sealants represent a good non-invasive alternative. However, although they work efficiently, their cost is high and they may not be available in all countries or regions. In addition, because commercial allogeneic fibrin sealant is obtained from human plasma, there is a risk of transmission of certain diseases and hypersensitive reactions may occur.

The safest way to prepare the fibrin sealant is to obtain it from the patient's own blood. Nevertheless, the preparation time (usually using freezing or lyophilization techniques) is long, requiring at least 24 hours for processing, so it cannot be done during surgery or it requires the patient to come the day before surgery to have blood extracted. These freezing or lyophilization techniques are based on achieving an increase in the concentration of fibrinogen and they suffer from limitations such as a low concentration of fibrinogen or coagulation proteins, so the sealing time is long and very variable due to the biological variability of each patient. Other methods used to expedite the preparation of an autologous fibrin sealant use chemicals to promote fibrinogen precipitation, but such products can irritate and inflame the tissues where they are applied.

This invention aims to achieve a formulation with desirable biological or medical properties, obtained from an initial blood composition which is rich in platelets and/or growth factors, which can be prepared in surgical time and with increased tissular adhesiveness. Among other applications, it is hoped that the formulation will serve as an alternative to commercial fibrin sealant.

BRIEF DESCRIPTION OF THE INVENTION

The object of the invention is a formulation with desirable biological or medical properties, which comprises or is derived from an initial blood composition (of human or animal origin; autologous, homologous or heterologous), rich in platelets and/or growth factors and comprising proteins from the initial blood composition itself, with the specific feature that the formulation has an increased adhesiveness. This formulation can be autologous (prepared from and applied to the same donor), homologous (the donor and the recipient are of the same species) or heterologous (the donor and the recipient are of different species) and could be qualified as a "fibrin sealant" (using a terminology analogous to that used to refer to the application of fibrin preparations for sealing) because it has an increased adhesiveness and accelerated coagulation.

The composition has a new morphological and biomechanical configuration compared to other fibrin sealants, platelet-rich blood compositions and/or growth factors, and similar products known in the prior art.

The formulation of this invention is biocompatible, biodegradable and has the desirable biological or medical properties provided by the presence of platelets or growth factors. In addition, the formulation has increased tissular adhesiveness and is produced quickly. The formulation according to this invention is therefore an advantageous alternative to conventional fibrin sealant, due to the fact that the formulation is autologous, adhesive and is obtained quickly without the addition of chemical substances. In addition, the formulation has a good compressive adhesiveness, similar to or better than the conventional allogeneic fibrin sealant Tisseel® and PRP (commonly used as a sealant), and adequately supports any resistance that a tissue can exert on it; therefore, the formulation is very suitable for use as a fibrin sealant. In addition, it is injectable.

The object of this invention is also to describe a method for the preparation of this formulation, wherein this method comprises the steps of: having an initial blood composition rich in platelets and/or growth factors whose base formulation may vary; heating the blood composition to a temperature of 40 to 55° C.; centrifuging the initial blood composition for at least 1 minute; and reducing the volume of the initial composition. This method according to the invention also comprises the addition of a platelet-activating substance and the formation of fibrin to obtain a blood composition rich in platelets and/or growth factors in gel form.

BRIEF DESCRIPTION OF DRAWINGS

The details of the invention can be seen in the accompanying figures, which are not intended to limit the scope of the invention.

DETAILED DESCRIPTION OF THE INVENTION

Figure 1:
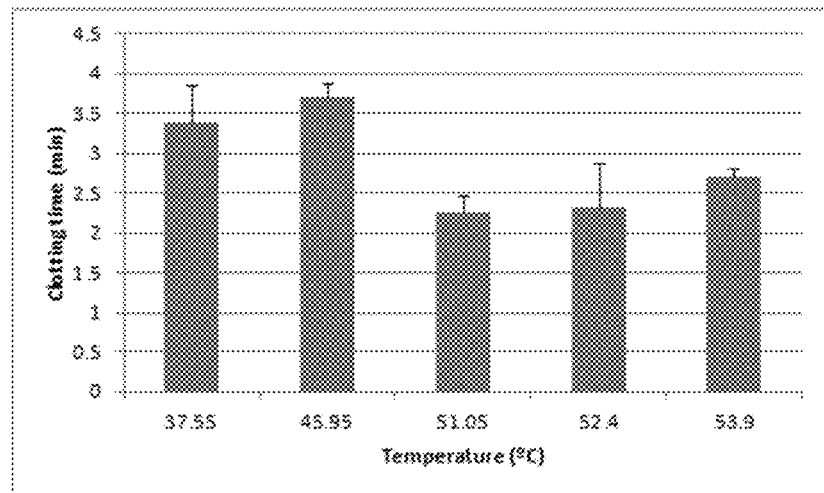
FIG. 1 shows the coagulation time of different examples of formulations according to the invention.

In order to overcome problems still existing in the prior art related to the adhesiveness of PRPs, an alternative formulation with desirable biological or medical properties and with improved adhesiveness is proposed. This formulation comprises or is derived from an initial blood composition containing platelets. This composition is adhesive as a result of heat treatment and the formation of a fibrin clot.

It has been found that the sealant prepared according to this invention has a tissular adhesiveness similar to the Tisseel® fibrin sealant and better than the adhesiveness of a platelet-rich plasma or conventional platelet-rich fibrin.

The initial blood composition could be, for example, a platelet-rich blood plasma, i.e., a plasma with a high concentration of platelets. This plasma has generally been obtained by the technique of centrifuging blood (to separate it into a red blood cell fraction, a white blood cell fraction and a platelet-rich plasma (PRP) fraction) and separating all or part of the fraction into platelet-rich plasma (PRP).

The initial blood composition may or may not contain leukocytes.

For the activation of the initial blood composition, one or more of the following can be used: calcium chloride, thrombin, sodium gluconate, collagen, supernatant (a liquid substance that appears above the clotted blood when coagulation of a platelet-rich plasma (PRP) and its subsequent retraction is caused), supernatant of a blood plasma rich in growth factors, or any other agent that acts by activating platelets and inducing fibrin formation so that the platelets release certain growth factors from within.

A method for the preparation of a formulation with desirable biological or medical properties is also proposed, wherein this method comprises the following steps:
  a) having an initial blood composition rich in platelets and/or growth factors with or without anticoagulant, which is preferably a platelet-rich plasma with or without leukocytes, or a plasma rich in growth factors with or without leukocytes,
  b) raising the temperature of the initial composition to a temperature of 40 to 55° C.,
  c) centrifuging the initial blood composition for at least 1 minute.
  d) removing at least part of the plasma fraction obtained as a result of centrifuging,
  e) activating the remaining blood composition after removing at least part of the plasma fraction as indicated in step d). Activation can be carried out, for example, by adding calcium chloride, thrombin, a combination of calcium chloride and thrombin, sodium gluconate, collagen, supernatant (a liquid substance that appears above the clotted blood when coagulation of a platelet-rich plasma (PRP) and its subsequent retraction is caused), supernatant of a blood plasma rich in growth factors and/or any other platelet-activating agent. As a result, platelet activation occurs and fibrin formation is induced so that platelets release certain growth factors from within.

This method produces a precipitation of protein substances without the denaturation of the fibrinogen as seen by the appearance of a fibrin clot after activation. By removing part of the volume of the initial composition, the concentration of these protein substances is increased. Moreover, the method produces a noticeable acceleration in the coagulation of the blood composition and its adhesive strength. In summary, as a result of the heating process, new biocompatible and biodegradable formulations are achieved, with two main advantages: a short coagulation time and a greater adhesiveness making this formulation suitable as a fibrin adhesive or sealant.

Preferably, the temperature of the initial blood composition is increased to a temperature in the range of 40 to 53° C.

The initial blood composition rich in platelets and/or growth factors may be of human or animal origin. In addition, it can be autologous (belonging to a patient who is to be subsequently treated with the final formulation), homologous (belonging to a member of the same species as the patient, patients, cells or other biological entity to be treated or processed with the final formulation) or heterologous (belonging to a member of a different species than the patient, patients, cells or other biological entity that is to be treated or processed with the final formulation).

The invention contemplates that the initial blood composition may optionally incorporate one or more additional substances, added prior to the heat treatment claimed. These additional substances may be:
- one or more bioactive agents selected from proteins, peptides, nucleic acids, polysaccharides, lipids, non-protein organic substances and inorganic substances;
- one or more biodegradable polymers selected from: hyaluronic acid, hyaluronate salts, chondroitin 4 sulphate, chondroitin 6 sulphate, dextran, silica gel, alginate, hydroxypropyl methylcellulose, chitin derivatives, preferably chitosan, xanthan gum, agarose; polyethylene glycol (PEG), polyhydroxyethylene methacrylate (HEMA), synthetic or natural proteins, and collagens;
- one or more organic polymers selected from the group of polycaprolactone, polyglycolic, polylactic, and their co-polymers;
- one or more of the following agents: antibiotics, antimicrobials, anticancer drugs, analgesics, growth factors, hormones;
- one or more inorganic component selected from the group of calcium salts, magnesium salts, and/or strontium salts.

The invention also contemplates the possibility that any of the above substances can be added to the formulation after the heat treatment has been carried out.

The formulation according to the invention contemplates various embodiments in which the formulation can comprise, in addition to the claimed technical aspects, other compounds, components, molecules, etc. that are convenient for the specific application for which the formulation will be intended.

In addition, it is possible to perform additional steps on the formulation produced according to the method described in this invention, including desiccation to increase its versatility; i.e., before its activation (platelet activation and fibrin formation), the formulation according to the invention can be dried (with dry heat) or lyophilized. This formulation can be subsequently rehydrated by different methods such as adding a saline solution, a platelet-rich plasma, a supernatant from a platelet-rich plasma, a plasma rich in growth factors, a supernatant from a plasma rich in growth factors, or any other liquid substance.

EXAMPLES

Example 1

This example starts with a sample of 9 airtight tubes (9 ml) that contain blood taken from a patient. The tubes are centrifuged at a speed of 580 g, for 8 minutes at room temperature. As a consequence of centrifuging, the blood contained in each tube divides into several fractions. The upper fraction, or fraction of platelet-rich plasma (PRP), is extracted to a white tube, obtaining a total of 36 ml of plasma. The plasma is divided into 6 tubes, each containing 6 ml of plasma. Then, the temperature of each of the 6 tubes is raised to 37.55, 45.95, 51.05, 52.4, 53.9 and 55.35° C., respectively. Subsequently, the 6 tubes are centrifuged at a speed of 580 g, for 8 minutes at room temperature, causing the precipitation of platelets and new protein substances. In order to concentrate these protein substances after centrifuging the heated plasma, the upper half of the plasma is removed. Finally, the precipitate is resuspended in the remaining plasma of the tube.

Next, the formulations in the 6 tubes are activated by adding a PRP supernatant (333 µl) and 20 µl of calcium per each 1 ml of formulation, which starts the formation of fibrin in the formulations.

The coagulation time (the time it takes for the blood composition to change its state from liquid to gel) due to fibrin formation was measured. FIG. 1 shows the capacity of the method of the invention to accelerate coagulation time. It should be noted that the coagulation time of a conventional PRP, activated in the same manner as the formulations according to the invention above (i.e., with PRP supernatant (333 µl) and 20 µl of calcium per each 1 ml) was 4.5 minutes. As can be seen in the graphic, the formulations according to the invention have lower or accelerated coagulation times compared to this conventional PRP. This acceleration of coagulation is greatest for the temperature of 51.05° C., followed by the temperatures of 52.4 and 53.9° C. A stable clot was not obtained at a temperature of 55.3° C.

Example 2

This example starts with a sample of 9 airtight tubes (9 ml) that contain blood taken from a patient. The blood is centrifuged at a speed of 580 g, for 8 minutes at room temperature. As a consequence of centrifuging, the blood contained in each tube is divided into several fractions. The upper fraction, or fraction of platelet-rich plasma (PRP), is extracted to a white tube, obtaining a total of 36 ml of plasma. The plasma is divided into 6 tubes, each containing 6 ml of plasma. Next, the temperature of each of the tubes is raised to 37.55, 45.95, 51.05, 52.4, 53.9 and 55.35° C., respectively. Subsequently, it is centrifuged at a speed of 580 g, for 8 minutes at room temperature, causing the precipitation of platelets and new protein substances. In order to concentrate these protein substances and after centrifuging the heated plasma, the upper half of the plasma is removed. Finally, the precipitate is resuspended in the remaining plasma remaining in the tube.

Then, the formulations in the 6 tubes are activated by adding a PRP supernatant (333 µl) and 20 µl of calcium per each 1 ml of formulation, which starts fibrin formation in the formulations.

Figure 2:
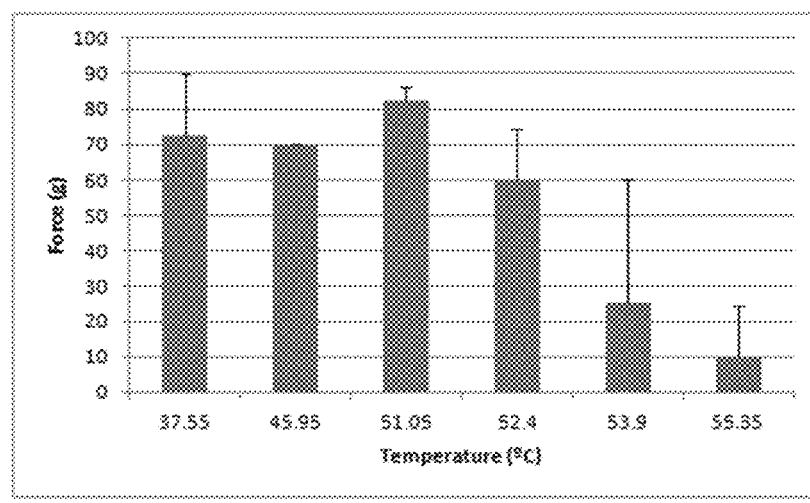
FIG. 2 shows the adhesiveness of different examples of formulations according to the invention.

Two glass slides were glued with the formulation after activation. After coagulation, the glued slides were incubated in distilled water for 3 minutes and then the strength of the adhesion of the formulation was measured using weights in grams. FIG. 2 shows the adhesive strength of the formulations. The highest adhesive strength is that corresponding to the temperature of 51.05° C., followed by the temperatures of 37.55 and 45.95° C. The lowest adhesive strength is for the temperature of 55.3° C., followed by the temperature of 53.9° C.

Example 3

This example starts with a sample of 9 airtight tubes (9 ml) that contain blood taken from a patient. The tubes are centrifuged at a speed of 580 g, for 8 minutes at room temperature. As a consequence of centrifuging, the blood contained in each tube divides into several fractions. The upper fraction, or fraction of platelet-rich plasma (PRP), is extracted to a white tube, obtaining a total of 36 ml of plasma. The plasma is divided into 6 tubes, each containing 6 ml of plasma. The samples are processed according to the following:

- Control sample: The PRP is activated with calcium ions in a ratio of 20 µl of 10% calcium chloride per each 1 ml of PRP.
- Activator control sample: The PRP is activated with PRP supernatant (333 µl) and 20 µl of 10% calcium chloride per each 1 ml of PRP.
- Method control sample: The PRP is centrifuged at a speed of 580 g, for 8 minutes at room temperature. ⅔ of the initial volume is removed and the platelet precipitate is resuspended in the remaining ⅓ of the initial volume. It is activated with PRP supernatant (333 µl) and 20 µl of 10% calcium chloride per each 1 ml of PRP.
- Formulation sample 1: The PRP temperature is raised to 51° C. Subsequently, it is centrifuged at a speed of 580 g, for 8 minutes at room temperature. ⅔ of the initial volume is removed and the platelet and protein precipitate is resuspended in the remaining ⅓ of the initial volume. The formulation is activated with PRP supernatant (333 µl) and 20 µl of 10% calcium chloride per each 1 ml of PRP.
- Formulation sample 2: The PRP temperature is raised to 51° C. Subsequently, it is centrifuged at a speed of 580 g, for 8 minutes at room temperature. ½ of the initial volume is removed and the platelet and protein precipitate is resuspended in the remaining ½ of the initial volume. The formulation is activated with PRP supernatant (333 µl) and 20 µl of 10% calcium chloride for every 1 ml of PRP.
- Formulation sample 3: The PRP temperature is raised to 51° C. Subsequently, it is centrifuged at a speed of 580 g, for 8 minutes at room temperature. The platelet and protein precipitate is resuspended in the total initial volume. The formulation is activated with PRP supernatant (333 µl) and 20 µl of 10% calcium chloride per each 1 ml of PRP.
- Formulation sample 4: The platelets of PRP are removed by means of filtration using filters with a pore size of 20 µl. Then the temperature of the PRP is raised to 51° C. Subsequently, it is centrifuged at a speed of 580 g, for 8 minutes at room temperature. ⅔ of the initial volume is removed and the platelet and protein precipitate is resuspended in the remaining ⅓ of the initial volume. The formulation is activated with PRP supernatant (333 µl) and 20 µl of 10% calcium chloride per each 1 ml of PRP.

Figure 3:
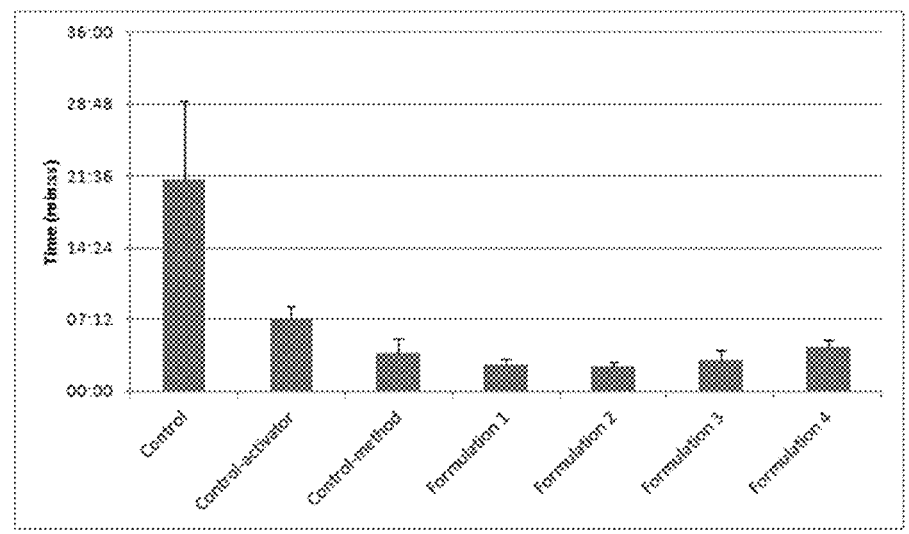
FIG. 3 shows the effect of the activator and platelets on the coagulation time of the formulations according to the invention.

The results of the coagulation time in FIG. 3 indicate that: the use of the thrombin activator (PRP supernatant)+calcium, used in the control-activator, control method and formulations 1-4, accelerates the coagulation of the PRP compared to the use of only calcium ions (control sample). Moreover, a second centrifuging of the PRP before activation (control method and formulations 1-4) further accelerates coagulation, possibly due to the increase in platelet concentration by removing part of the initial volume. However, the method according to the invention accelerates coagulation independently of the platelet concentration as shown by the results of formulation 3 (without increase in platelet concentration) and formulation 4 (without platelets). The shortest coagulation times were those corresponding to formulations 1 and 2. Thus the coagulation time indicates the innovation and efficacy of the method of the invention for accelerating the coagulation process.

Example 4

This example starts with a sample of 9 airtight tubes (9 ml) that contain blood taken from a patient. The tubes are centrifuged at a speed of 580 g, for 8 minutes at room temperature. As a consequence of centrifuging, the blood contained in each tube divides into several fractions. The upper fraction, or fraction of platelet-rich plasma (PRP), is extracted to a white tube, obtaining a total of 36 ml of plasma. The plasma is divided into 6 tubes, each containing 6 ml of plasma. Samples are processed according to the following:

- Control sample: The PRP is activated with calcium ions in a ratio of 20 µl of 10% calcium chloride per each 1 ml of PRP.
- Activator control sample: The PRP is activated with PRP supernatant (333 µl) and 20 µl of 10% calcium chloride per each 1 ml of PRP.
- Method control sample: The PRP is centrifuged at a speed of 580 g, for 8 minutes at room temperature. ⅔ of the initial volume is removed and the platelet precipitate is resuspended in the remaining ⅓ of the initial volume. It is activated with PRP supernatant (333 µl) and 20 µl of 10% calcium chloride per each 1 ml of PRP.
- Formulation sample 1: The PRP temperature is raised to 51° C. Subsequently, it is centrifuged at a speed of 580 g, for 8 minutes at room temperature. ⅔ of the initial volume is removed and the platelet and protein precipitate is resuspended in the remaining ⅓ of the initial volume. The formulation is activated with PRP supernatant (333 µl) and 20 µl of 10% calcium chloride per each 1 ml of PRP.
- Formulation sample 2: The PRP temperature is raised to 51° C. Subsequently, it is centrifuged at a speed of 580 g, for 8 minutes at room temperature. ½ of the initial volume is removed and the platelet and protein precipitate is resuspended in the remaining ½ of the initial volume. The formulation is activated with PRP supernatant (333 µl) and 20 µl of 10% calcium chloride per each 1 ml of PRP.
- Formulation sample 3: The PRP temperature is raised to 51° C. Subsequently, it is centrifuged at a speed of 580 g, for 8 minutes at room temperature. The platelet and protein precipitate is resuspended in the total initial volume. The formulation is activated with PRP supernatant (333 µl) and 20 µl of 10% calcium chloride per each 1 ml of PRP.
- Formulation sample 4: The platelets of PRP are removed by means of filtration with filters of 20 µl pore size. Then the temperature of the PRP is raised to 51° C. Subsequently, it is centrifuged at a speed of 580 g, for 8 minutes at room temperature. ⅔ of the initial volume is removed and the platelet and protein precipitate is resuspended in the remaining ⅓ of the initial volume. The formulation is activated with PRP supernatant (333 µl) and 20 µl of 10% calcium chloride per each 1 ml of PRP.

Figure 4:
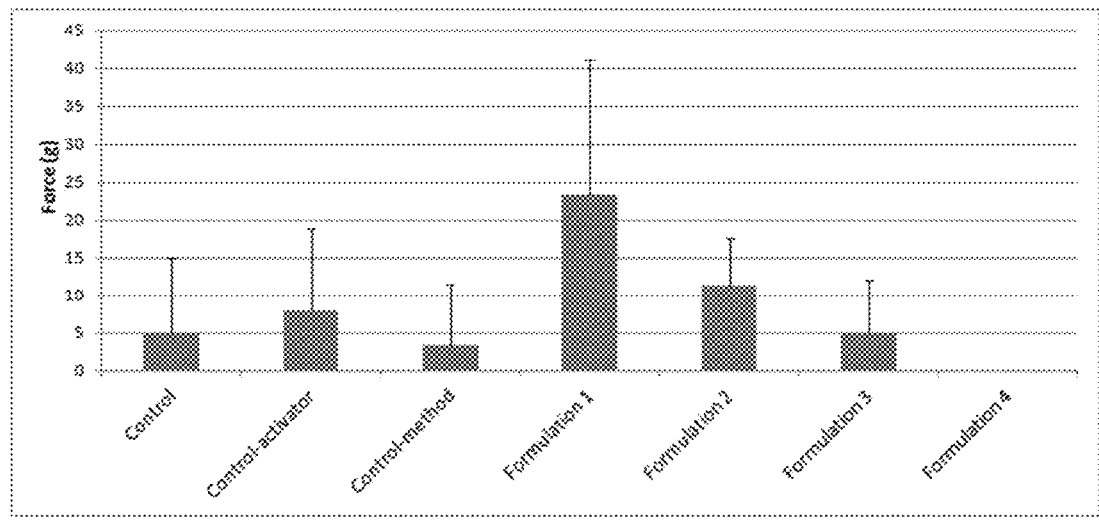
FIG. 4 shows the effect of the activator and platelets on the adhesiveness of different examples of formulations according to the invention.

Two glass slides were glued together with the samples described above after activation. The samples were incubated in distilled water and then the strength of the formulation adhesiveness was measured using weights in grams. FIG. 4 shows the adhesive strength of the formulations. The results clearly indicate that the improvement in adhesion occurs only in the formulations according to the present invention (formulations 1 and 2) since the use of thrombin+ calcium (activator control) or a increased platelet concentration (method control) did not improve the adhesion of activated PRP with calcium ions. The best adhesion was obtained by formulations 1 and 2 of the present invention.

Example 5

This example starts with a sample of 8 airtight tubes (9 ml) that contain blood taken from a patient. The tubes are centrifuged at a speed of 580 g, for 8 minutes at room temperature. As a consequence of centrifuging, the blood contained in each tube divides into several fractions. The upper fraction, or fraction of platelet-rich plasma (PRP), is extracted to a white tube, obtaining a total of 30 ml of plasma. The plasma is divided into 5 tubes, each containing 6 ml of plasma. The samples are processed according to the following:

Activator control sample: The PRP is activated with PRP supernatant (333 µl) and 20 µl of 10% calcium chloride per each 1 ml of PRP.

Formulation sample 1: The PRP temperature is raised to 51° C. Subsequently, it is centrifuged at a rate of 580 g, for 8 minutes at room temperature. ⅔ of the initial volume is removed and the platelet and protein precipitate is resuspended in the remaining ⅓ of the initial volume. The formulation is activated with PRP supernatant (333 µl) and 20 µl of 10% calcium chloride per 1 ml of PRP.

Formulation sample 2: The PRP temperature is raised to 51° C. Subsequently, it is centrifuged at a rate of 580 g, for 8 minutes and at room temperature. ½ of the initial volume is removed and the platelet and protein precipitate resuspended in the remaining ½ of the initial volume. The formulation is activated with the following ratios of activator/formulation volume:
1. PRP supernatant (333 µl) and 20 µl of 10% calcium chloride per each 1 ml of PRP (formulation 2).
2. PRP supernatant (235.8 µl) and 14.2 µl of 10% calcium chloride per each 1 ml of PRP (formulation 2 A)
3. PRP supernatant (166.7 µl) and 10 µl of 10% calcium chloride per each 1 ml of PRP (formulation 2 B)

Tisseel® Sample: A Tisseel® commercial adhesive and sealant (Baxter S. L., Valencia, Spain) was purchased and used according to the manufacturer's instructions.

Figure 5:
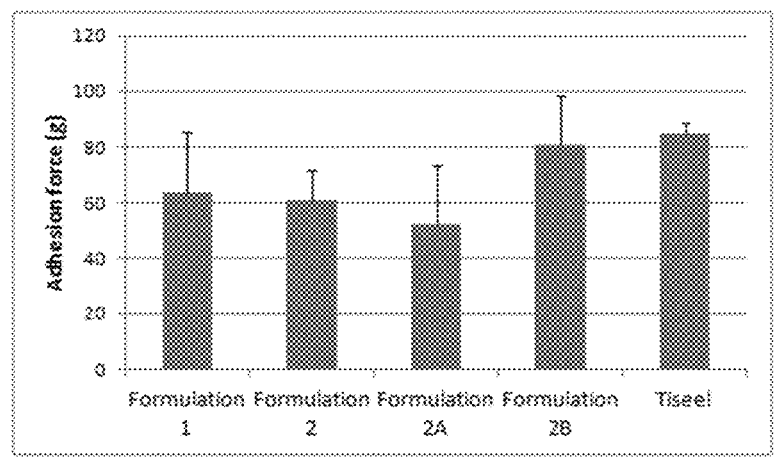
FIG. 5 shows the effect of the activator and the effectiveness of different examples of formulations according to the invention and in comparison with the commercial sealant Tisseel® in adhesiveness.

Two glass slides were glued using the samples previously described after activation. The samples were incubated in distilled water and then the adhesive strength of the formulation was measured using weights in grams. FIG. 5 shows that the adhesive strength of the formulations according to the present invention can also be improved by optimising the volume of added activator (Formulation 2B). The results also show that the adhesive strength of the formulation according to the invention (Formulation 2 B) is comparable with the commercial sealant Tisseel®.

Example 6

This example starts with a sample of 7 airtight tubes (9 ml) containing blood drawn from a patient. The tubes are centrifuged at a rate of 580 g, for 8 minutes at room temperature. As a result of centrifuging, the blood contained in each tube divides into several fractions. The upper fraction, or platelet-rich plasma (PRP) fraction, is extracted into a white tube, resulting in a total of 24 ml of plasma. The plasma is divided into 4 tubes, each containing 6 ml of plasma. Samples are processed according to the following:

Activator control sample: The PRP is activated with PRP supernatant (333 µl) and 20 µl of 10% calcium chloride per each 1 ml of PRP.

Formulation sample 1: The PRP temperature is raised to 51° C. Subsequently, it is centrifuged at a rate of 580 g, for 8 minutes and at room temperature. ⅔ of the initial volume is removed and the platelet and protein precipitate is resuspended in the remaining ⅓ of the initial volume. The formulation is activated with PRP supernatant (333 µl) and 20 µl of 10% calcium chloride per each 1 ml of PRP.

Formulation sample 2: The PRP temperature is raised to 51° C. Subsequently, it is centrifuged at a rate of 580 g, for 8 minutes and at room temperature. ½ of the initial volume is removed and the platelet and protein precipitate is resuspended in the remaining ½ of the initial volume. The formulation is activated with the following ratios of activator/formulation volume:
1. PRP supernatant (333 µl) and 20 µl of 10% calcium chloride per each 1 ml of PRP (formulation 2).
2. PRP supernatant (166.7 µl) and 10 µl of 10% calcium chloride per each 1 ml of PRP (formulation 2 B)

Tisseel® Sample: A Tisseel® commercial adhesive and sealant (Baxter S. L., Valencia, Spain) was purchased and used according to the manufacturer's instructions.

Figure 6:
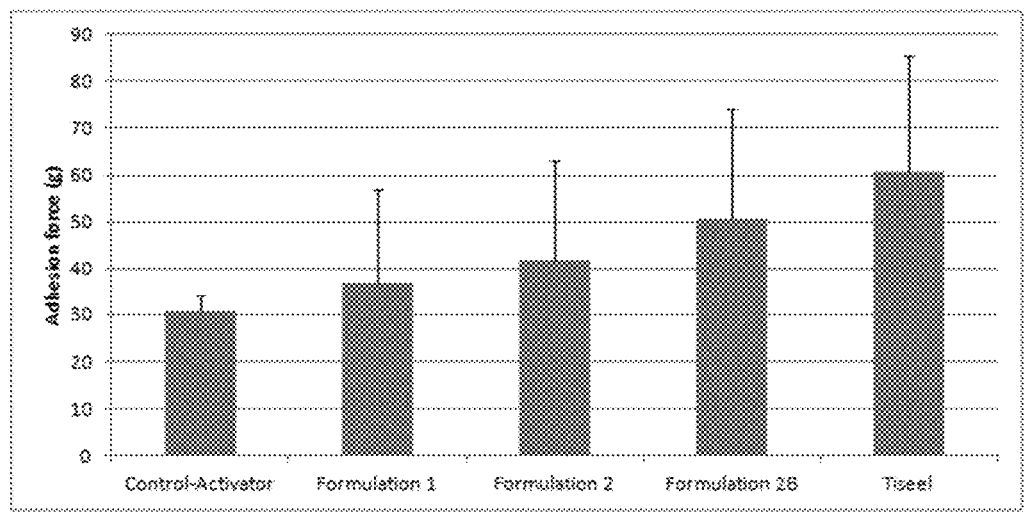
FIG. 6 shows the effectiveness as a tissular adhesive of different examples of formulations according to the invention compared to the commercial sealant Tisseel® as a tissular adhesive.

Biological samples of pig skin were prepared. The skin samples were glued to a support using a universal adhesive. Two skin specimens were then glued to the samples previously described. The strength of the adhesion of the formulation was then measured using weights in grams and hanging the weights on the support of a skin specimen. FIG. 6 shows the novelty and effectiveness of the invention in improving the adhesive strength and that the adhesive capacity can be further increased by optimizing the volume of added activator (Formulation 2 B). The results also indicate that the adhesive strength of the formulation according to the present invention (Formulation 2 B) is comparable to the adhesive strength of the commercial sealant Tisseel®.

The invention claimed is:
1. A method for the preparation of an adhesive formulation from an initial blood composition, comprising:
   a) obtaining an initial blood composition, of human or animal origin, containing platelets;
   b) raising the temperature of the initial blood composition to a temperature of 40 to 53° C.; and
   c) activating the platelets and forming a fibrin-containing formulation comprising a fibrin clot with a coagulation time lower than 4.5 minutes.
2. The method, according to claim 1, wherein the initial blood composition is a platelet-rich blood plasma.
3. Method, according to claim 1, wherein the initial blood composition is a blood plasma rich in released growth factors.
4. Method, according to claim 1, further comprising an additional step of centrifuging the blood composition after step b).
5. Method, according to claim 4, further comprising an additional step of removing part of the volume of the initial composition after step b).
6. Method, according to claim 1, wherein the step of activating platelets comprises adding at least one of the following: calcium chloride, thrombin, sodium gluconate, collagen, blood plasma supernatant, and blood plasma supernatant rich in growth factors.

7. Method, according to claim 1, wherein the formulation comprises one or more bioactive agents selected from proteins, peptides, nucleic acids, polysaccharides, lipids, non-protein organic substances and inorganic substances.

8. Method, according to claim 1, wherein the formulation comprises one or more biodegradable polymers selected from the following: hyaluronic acid, hyaluronate salts, chondroitin 4 sulphate, chondroitin 6 sulphate, dextran, silica gel, alginate, hydroxypropylmethylcellulose, derivatives of chitin, preferably chitosan, xanthan gum, agarose; glycolic polyethylene (PEG), polyhydroxyethylene methacrylate (HEMA), synthetic or natural proteins, collagens.

9. Method, according to claim 1, wherein the formulation comprises one or more organic polymers selected from the group of polycaprolactone, polyglycolic, polylactic, and their co-polymers.

10. Method, according to claim 1, wherein the formulation comprises one or more of the following agents: antibiotics, antimicrobials, anticancer drugs, analgesics, growth factors, hormones.

11. Method, according to claim 1, wherein the formulation comprises one or more inorganic components selected from the group of calcium salts, magnesium salts, and/or strontium salts.

\* \* \* \* \*